(12) United States Patent
Tao

(10) Patent No.: US 9,142,115 B2
(45) Date of Patent: Sep. 22, 2015

(54) METHOD AND DEVICE FOR DETECTING FATIGUE

(75) Inventor: Teh-Ho Tao, Zhunan Township, Miaoli County (TW)

(73) Assignee: HOLUX TECHNOLOGY INC., Hsinchu (TW)

(*) Notice: Subject to any disclaimer, the term of this patent is extended or adjusted under 35 U.S.C. 154(b) by 541 days.

(21) Appl. No.: 13/542,018

(22) Filed: Jul. 5, 2012

(65) Prior Publication Data

US 2013/0027208 A1    Jan. 31, 2013

(30) Foreign Application Priority Data

Jul. 26, 2011   (TW) .............................. 100126432 A

(51) Int. Cl.
*G08B 23/00* (2006.01)
*G08B 21/06* (2006.01)
*B60K 28/06* (2006.01)

(52) U.S. Cl.
CPC .............. *G08B 21/06* (2013.01); *B60K 28/06* (2013.01)

(58) Field of Classification Search
CPC .......... A61B 5/18; A61B 5/01; A61B 5/0205; A61B 5/4809; A61B 5/1118; A61B 5/7267; A61B 5/02055; A61B 5/7278; A61B 5/4812; A61B 5/7275; A61B 5/0816; A61B 5/7282; A61B 5/024; A61B 5/486; A61B 5/1103; G08B 21/06; G08B 21/02; B60W 2540/22; B60W 50/14; B60K 28/06; B60K 28/066
USPC ................. 340/575, 573.1, 576, 540; 73/760; 382/100, 103; 600/300, 504, 529, 481, 600/500

See application file for complete search history.

(56) References Cited

U.S. PATENT DOCUMENTS

| | | | |
|---|---|---|---|
| 5,573,006 A * | 11/1996 | Shimotani et al. ............ | 600/558 |
| 6,426,702 B1 | 7/2002 | Young et al. | |
| 6,822,573 B2 | 11/2004 | Basir et al. | |
| 7,027,621 B1 | 4/2006 | Prokoski | |
| 8,652,041 B2 * | 2/2014 | Moore-Ede ................... | 600/301 |
| 2003/0199943 A1 * | 10/2003 | Katz et al. ....................... | 607/48 |
| 2004/0193068 A1 * | 9/2004 | Burton et al. ................. | 600/544 |
| 2006/0293602 A1 * | 12/2006 | Clark ............................ | 600/500 |

* cited by examiner

*Primary Examiner* — Kerri McNally
(74) *Attorney, Agent, or Firm* — Muncy, Geissler, Olds & Lowe, P.C.

(57) ABSTRACT

A method for detecting fatigue is provided herein. The present invention includes the following steps: measuring a plurality of physiological feature data from a user in continuous time to generate a feature sequence; computing the rate of drop and/or calculating the difference of the rate of drop based on the feature sequence; and determining the fatigue level of the user by analyzing the rate of drop and the difference of the rate of drop. A fatigue detecting device is also disclosed here. The present invention can be utilized to effectively monitor the fatigue level of the user.

24 Claims, 7 Drawing Sheets

Difference

Accumulated time (10sec)

METHOD AND DEVICE FOR DETECTING FATIGUE

BACKGROUND OF THE INVENTION

1. Field of the Invention

The present invention relates to a technique of detecting fatigue, and more particularly to a method and device for detecting fatigue.

2. Description of the Prior Art

In recent years, death from overwork occurs more frequently because of high-pressure work, insufficient rest and lacking regular exercise especially for young adults. Besides, incidence of traffic accidents caused by driver fatigue is increasing. It has gradually become an important issue for industry to develop a method for detecting fatigue level of drivers before driving for preventing traffic accidents.

According to U.S. Pat. No. 7,027,621, it provides a method using infrared imaging of the driver's face and other body parts to assess potential risk so as to send a warning message. U.S. Pat. No. 6,426,702 alternatively provides a device by detecting eye and head movement to judge if vehicle operators are in fatigue. For U.S. Pat. No. 6,822,573, it offers a steering wheel with heart rate sensors arranged thereon and users must grab the steering wheel precisely and tightly to be detected. From those patents described above, precision may be doubted because optical sensors may lose alignment when vehicles are moving; sensors on the steering wheel require users to continuously holding the wheel and thus restrict users' movement. Therefore, a more accurate method must be developed to detect drivers' fatigue level.

SUMMARY OF THE INVENTION

The present invention is directed to a method and device for detecting fatigue; the fatigue level of users can be detected by analyzing the rate of drop and the difference of the rate of drop, wherein the rate of drop and the difference of the rate of drop are computed based on the feature sequence generated from the physiological feature data measured by the device.

A method for detecting fatigue according to an embodiment of the present invention comprises the following steps: measuring a plurality of physiological feature data from a user in continuous time to generate a feature sequence; computing a feature curve based on the feature sequence; computing a rate of drop based on the feature curve; determining whether a first condition is met, wherein the first condition is that the rate of drop is larger than a threshold for a first duration; and determining the fatigue level of the user depending on the first condition.

An device for detecting fatigue according to another embodiment of the present invention comprises: a measuring unit, for measuring a plurality of physiological feature data from a user in continuous time to generate a feature sequence; a memory unit, for storing the feature sequence; a computing unit, electrically connected to the measuring unit and the memory unit, for computing a feature curve based on the feature sequence and computing a rate of drop based on the feature curve; the computing unit determines whether a first condition is met for obtaining a detection result of the fatigue level of a user, wherein the first condition is that the rate of drop is larger than the threshold for a first duration; and an output unit, electrically connected to the computing unit, for outputting the detection result of the fatigue level.

The objective, technologies, features and advantages of the present invention will become more apparent from the following description in conjunction with the accompanying drawings, wherein certain embodiments of the present invention are set forth by way of illustration and examples.

BRIEF DESCRIPTION OF THE DRAWINGS

The foregoing aspects and many of the accompanying advantages of this invention will become more readily appreciated as the same becomes better understood by reference to the following detailed description, when taken in conjunction with the accompanying drawings, wherein.

DESCRIPTION OF THE PREFERRED EMBODIMENT

The detail description is provided below and the preferred embodiments described are only over the purpose of description rather than for limiting the present invention.

Figure 1:
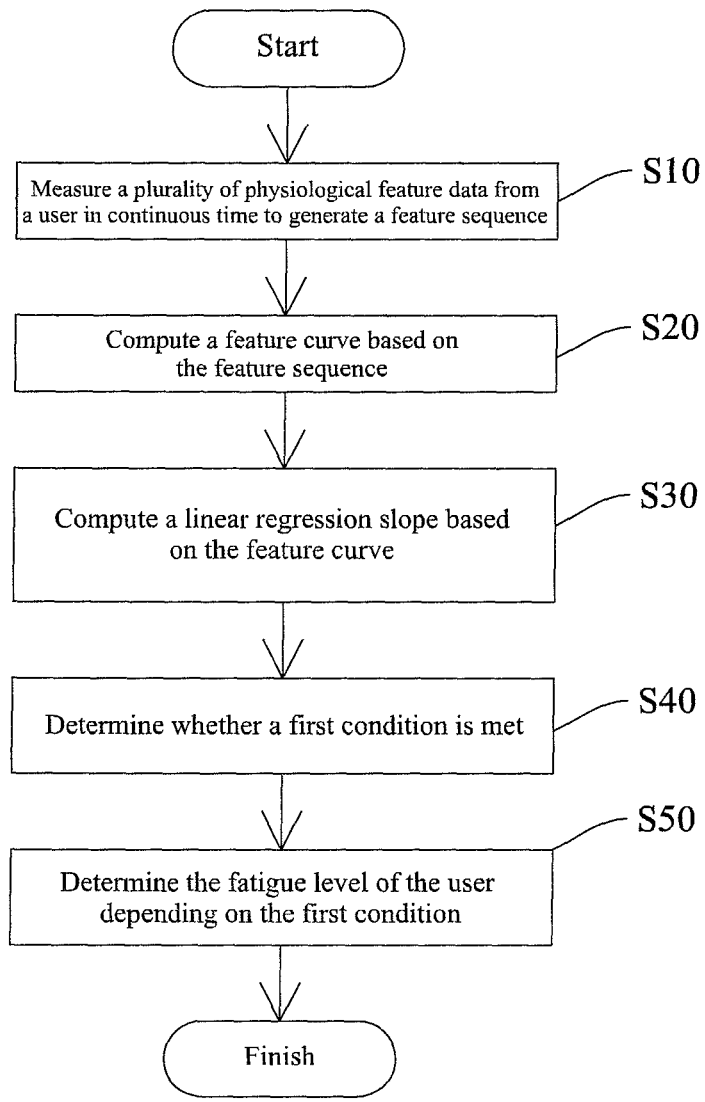
FIG. 1 is a flowchart illustrating a method for detecting fatigue according to an embodiment of the present invention.

FIG. 1 illustrates a method for detecting fatigue according to an embodiment of the present invention. In this embodiment, a method for detecting fatigue comprises the following steps: firstly, measuring a plurality of physiological feature data from a user in continuous time to generate a feature sequence (Step S10); secondly, computing a feature curve based on the feature sequence (Step S20); thirdly, computing a rate of drop based on the feature curve (Step S30); after that, determining whether the first condition is met, wherein the first condition is that the rate of drop is larger than a threshold for a first duration (Step S40); finally, determining the fatigue level of the user depending on the first condition (Step S50).

Continuing the above description, in one embodiment, a feature sequence can be generated from data of pulse frequency of cardiovascular circulation, for example, heart rate or pulse rate; the data can be sensed from a wire or wireless heartbeat sensor in the form of heart rate per minute updated every second ($HR_1$) or pulse rate per minute updated every second. The method for updating data is using the concept of moving average by averaging successive shifting sets of numbers within a time unit. Take heart rate for example, a feature curve can be a curve of heart rate, which is derived from $HR_{10}$, the average heart rate counted per ten seconds. Each data point on the $HR_{10}$ curve is calculated by averaging most recent ten successive $HR_1$s. Correspondingly, average values counted per minute or per five minutes mentioned hereinafter refer to a time unit of one minute or five minutes.

Figure 2A:
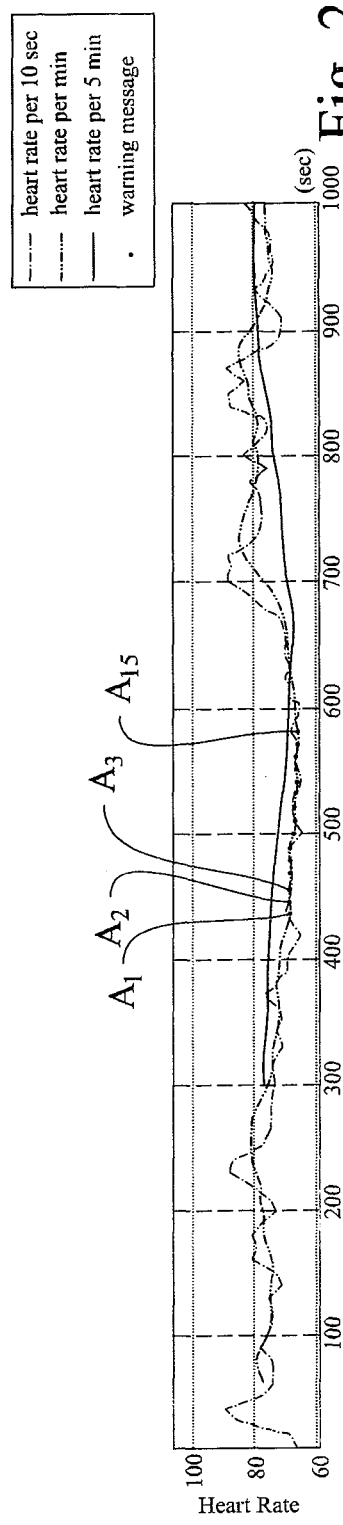
FIG. 2A, FIG. 2B and FIG. 2C are diagrams recording detection data of fatigue according to an embodiment of the present invention.
Figure 2B:
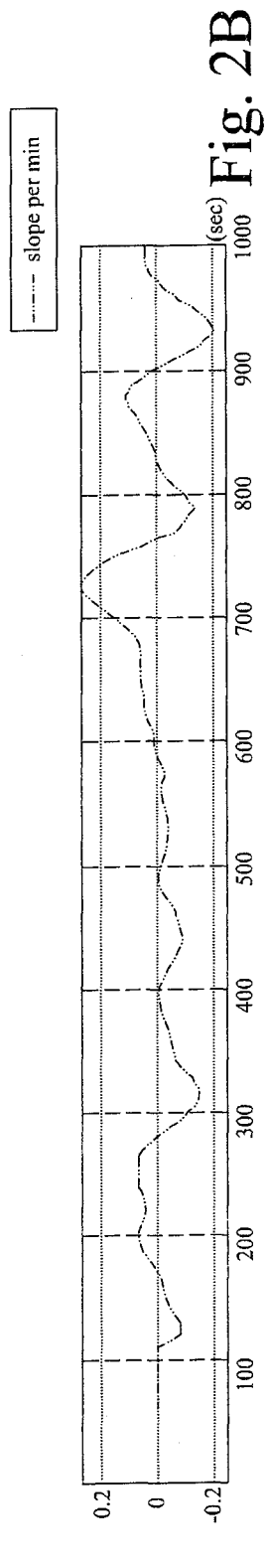
Figure 2C:
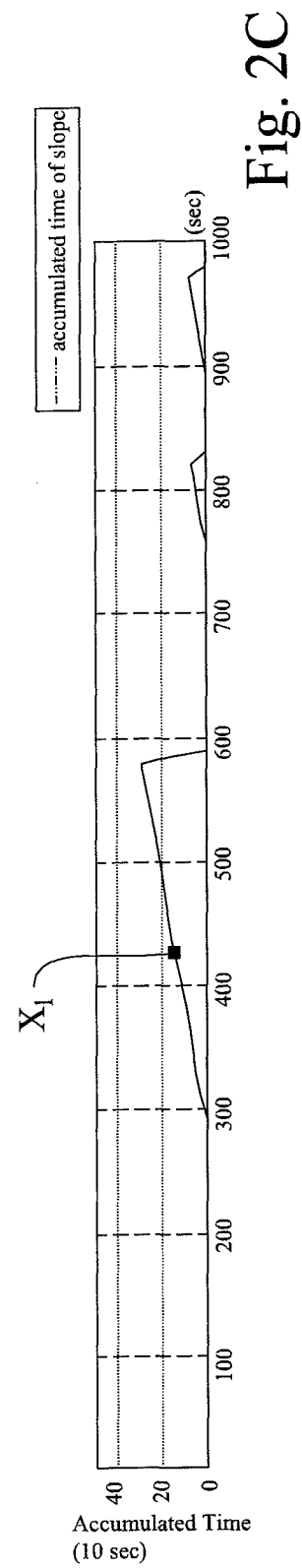

Referring to FIG. 2A, FIG. 2B and FIG. 2C, these are diagrams recording data of fatigue detection according to an embodiment of the present invention; in the first embodiment, a feature curve can be generated from $HR_{10}$ and $HR_{60}$, respectively corresponding to the average heart rate counted per ten seconds and per minute, wherein $HR_{10}$ and $HR_{60}$ can be updated as mentioned before. Therefore, an average value of the rate of drop, i.e. an average linear regression slope counted per minute for some embodiments (as shown in FIG. 2B), can be computed based on the feature curve; when the average linear regression slope is less than −0.05 (a threshold), the duration thereof is recorded. In the first embodiment, when the average linear regression slope counted per minute is less than −0.05 for at least 150 seconds (first duration), referring to the point $X_1$ in FIG. 2C, which means the user is in the condition of fatigue and a first warning message is generated (warning message $A_1$ as shown in FIG. 2A). If the situation as $X_1$ continues, warning messages will be generated continuously to remind users (warning messages $A_2$, $A_3$ ... $A_{15}$, as shown in the FIG. 2A) until the situation changes.

Figure 2D:
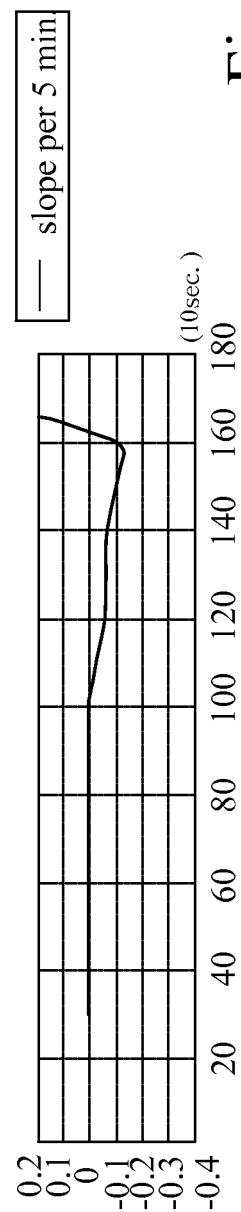
FIG. 2D, FIG. 2E and FIG. 2F are diagrams recording detection data of fatigue according to another embodiment of the present invention.
Figure 2E:
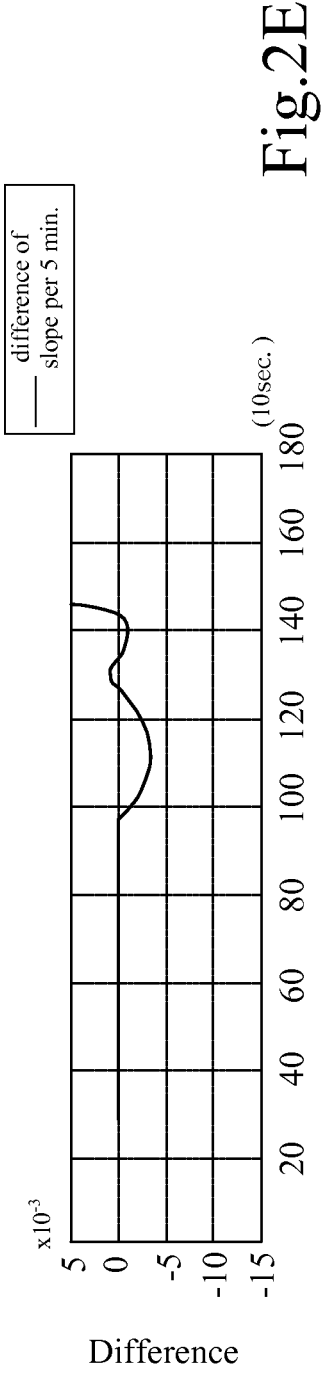
Figure 2F:
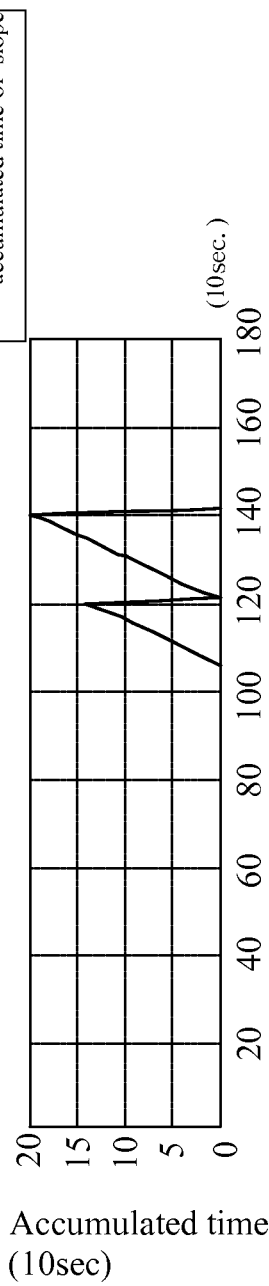
Figure 3:
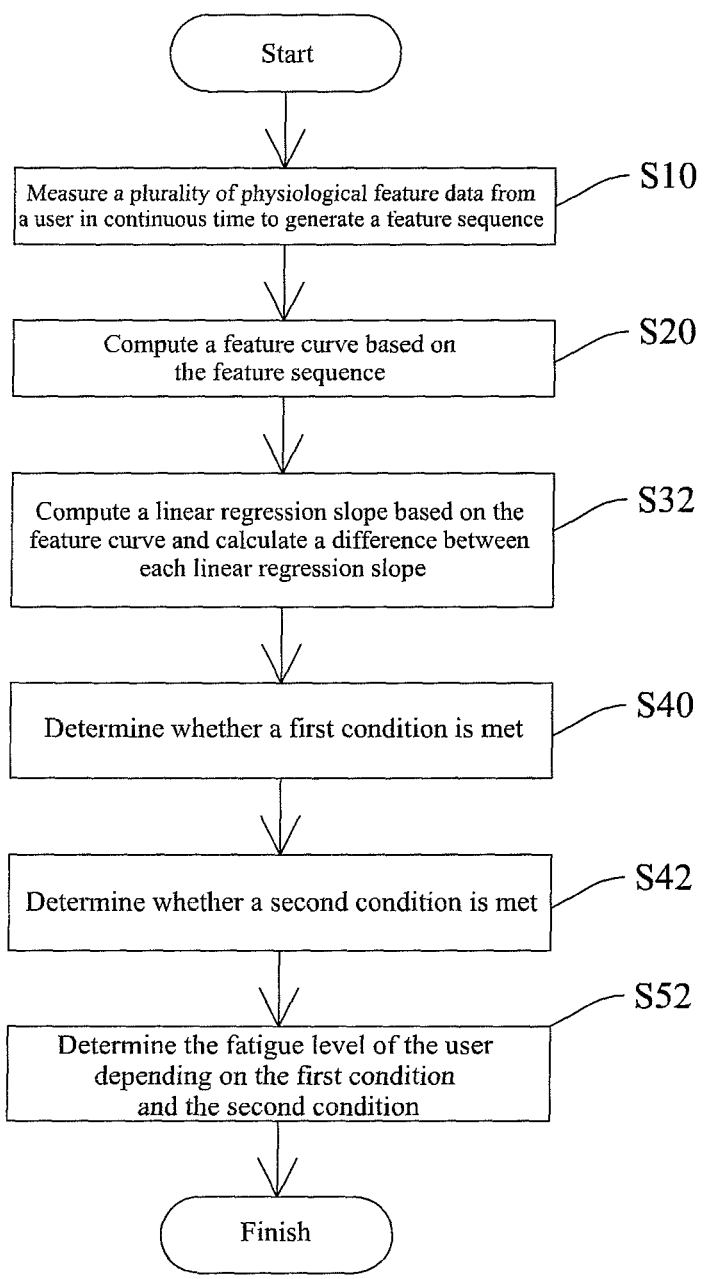
FIG. 3 is a flowchart illustrating a method for detecting fatigue according to an embodiment of the present invention.

In another embodiment, referring to the flowchart FIG. 3 and the diagrams recording data of fatigue detection (FIG. 2A, FIG. 2D, FIG. 2E and FIG. 2F); firstly referring to FIG. 2A, the difference between this embodiment and last embodiment is that the linear regression slope of this embodiment is an average slope counted per five minutes (as shown in FIG. 2D) and this embodiment further comprises calculating a difference of the rate of drop, i.e. difference between successive linear regression slope based on the feature curve for some embodiments (as shown in FIG. 2E and Step S32). After that, not only a first condition (Step S40) but also a second condition (Step S42) should be determined whether it is met, wherein the second condition is that whether the difference falls within a threshold interval for a second duration. Finally, fatigue level of users can be determined depending on the first condition and the second condition (Step S52), wherein a second warning message is generated when the first condition and the second condition are met.

Continuing the above description, in the foregoing embodiment, the first condition is that the average linear regression slope counted per five minutes is less than 0 for at least 140 seconds (first duration), which indicates that the heart rate of the user has continuously dropped for a period of time. Furthermore, the second condition is that the linear regression slope is less than 0 and the difference between successive linear regression slope falls within a threshold interval, for example, greater than −0.001 and less than 0.004, and lasted for the second duration (e.g. equal or more than 60 seconds), which indicates that the heart rate of the user has continuously dropped for a period of time and the dropping rate is approaching a constant value for the second duration of time, and the user is in the condition of losing concentration. A second warning message will be generated, for example, a warning message of lacking concentration of the user will be displayed for reminding users to concentrate on traffic safety.

Figure 4:
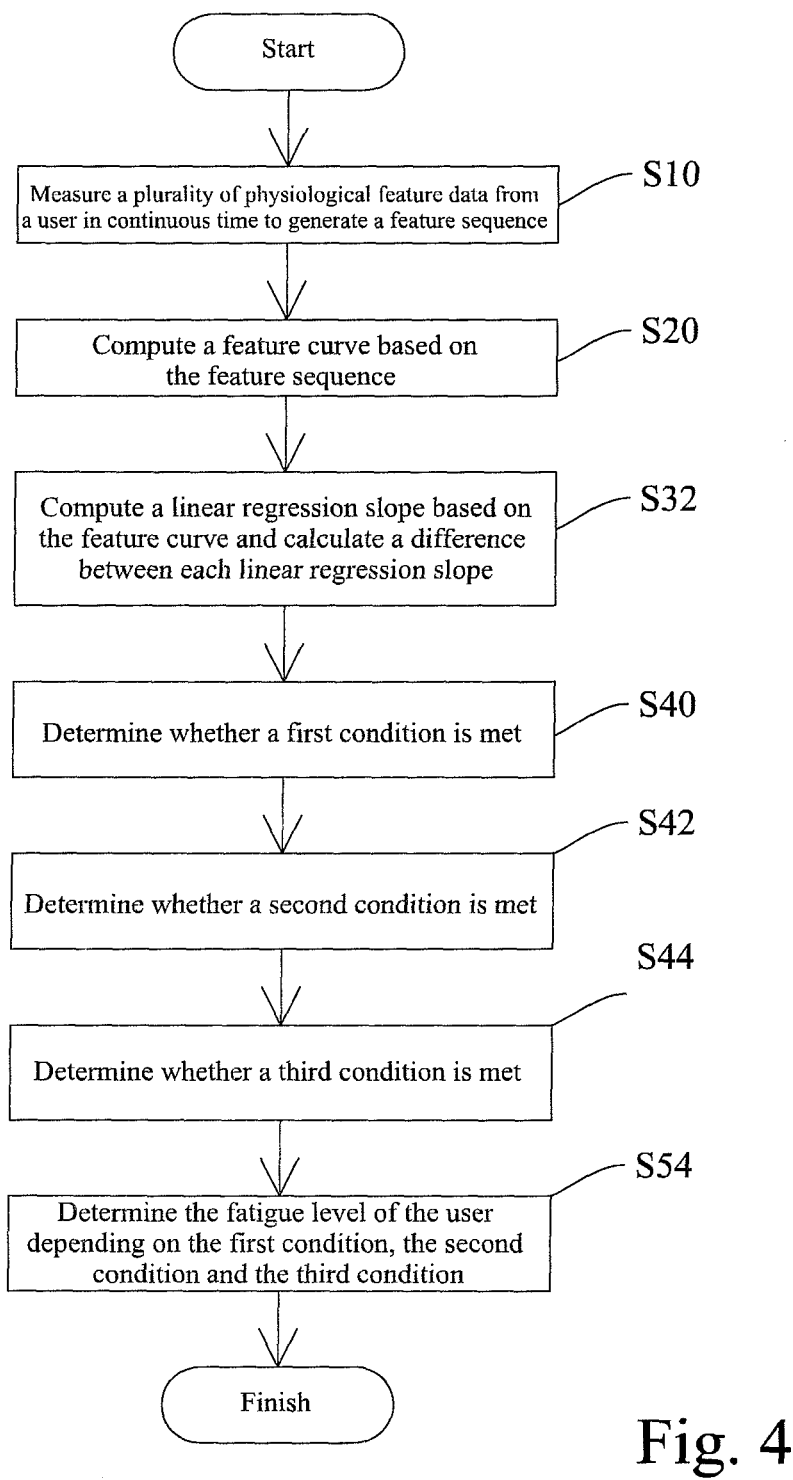
FIG. 4 is a flowchart illustrating a method for detecting fatigue according to an embodiment of the present invention.

As shown in the flowchart FIG. 4 according to the another embodiment and based on the last embodiment, the detecting method of the present invention further comprises that whether a third condition is met, wherein the third condition is that the linear regression slope is less than 0 and the difference between successive linear regression slope falls within the threshold interval for a third duration (Step S44); finally, determining fatigue level of users depending on the first condition, the second condition and the third condition (Step S54), wherein a third warning message is generated when the first condition and the third condition are met, and the third condition is approximately the same as the last embodiment except the difference of length between the second duration and the third duration. In this embodiment, the third duration is equal or greater than 90 seconds, or at least 30 seconds greater than the second duration. In other words, the third condition is to determine whether these computed values fall within the threshold interval for enough time and the third warning message aims to inform the user of fatigue status.

A method for detecting fatigue according to an embodiment of the present invention can be applied to detecting drivers. Take a feature sequence for example, when the first condition and the second condition are met, it represents heart rate of a user has continuously dropped for a period of time with a following phase in which the dropping rate of user's heart rate is approaching a constant value for a period of time, which indicates the user is in the condition of losing concentration; a warning message is therefore generated to remind the user to concentrate on traffic safety. When the first condition and the third condition are met, it represents heart rate of a user has continuously dropped for a period of time with a following long period of time in which the dropping rate of heart rate is approaching a constant value, which indicates the user is in fatigue status and a warning message is therefore generated to warn the user to stop driving for preventing risk. Using the measured result of feature sequence and analyzing and interpreting the linear regression slop and the difference between successive linear regression slope can effectively monitor fatigue level of users.

Figure 5:
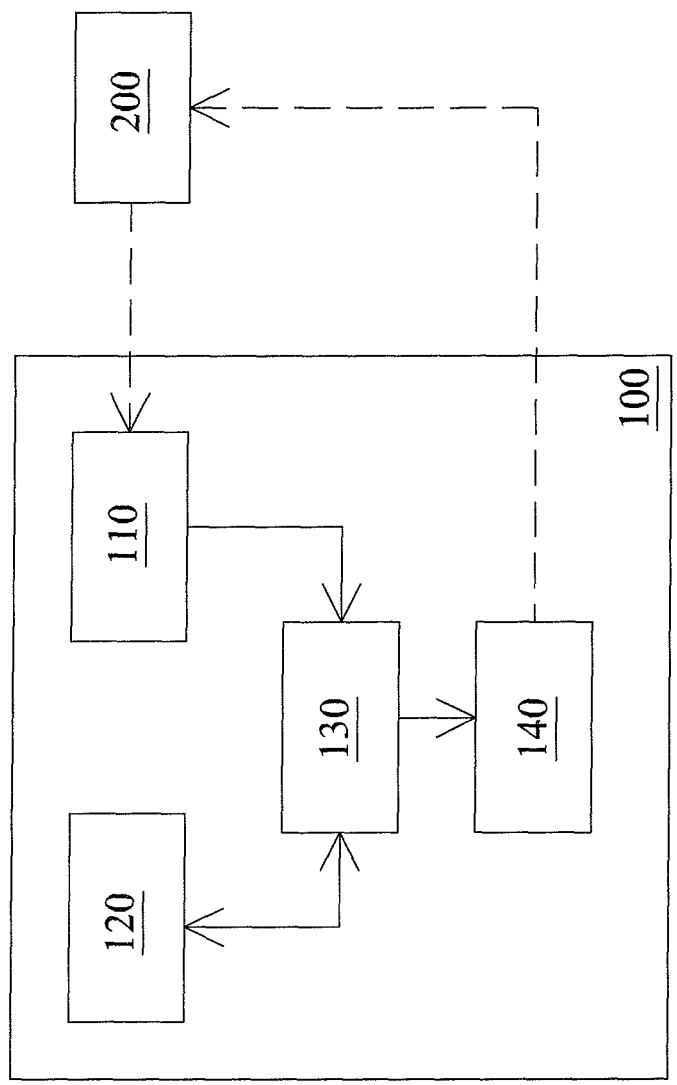
FIG. 5 is a schematic diagram illustrating a device for detecting fatigue according to an embodiment of the present invention.

FIG. 5 is a schematic diagram illustrating a device for detecting fatigue according to another embodiment of the present invention, wherein a device for detecting fatigue 100 comprises: a measuring unit 110, for measuring a plurality of physiological feature data from a user 200 in continuous time to generate a feature sequence; a memory unit 120, for storing the feature sequence; a computing unit 130, electrically connected to the measuring unit 110 and the memory unit 120, for computing a feature curve based on the feature sequence, and computing a linear regression slope and/or simultaneously calculating a difference between each linear regression slope based on the feature curve; the computing unit 130 determines whether at least one of a first condition, a second condition and a third condition is met for obtaining a detection result of the fatigue level of a user, wherein the determining standards and range of thresholds in respect of the first condition, the second condition and the third condition are described hereinbefore and are not elaborated any longer; and an output unit 140, electrically connected to the computing unit 130, for outputting the detection result of the fatigue level, wherein the output unit 140 can be at least one of a display screen or a sound device.

Figure 6:
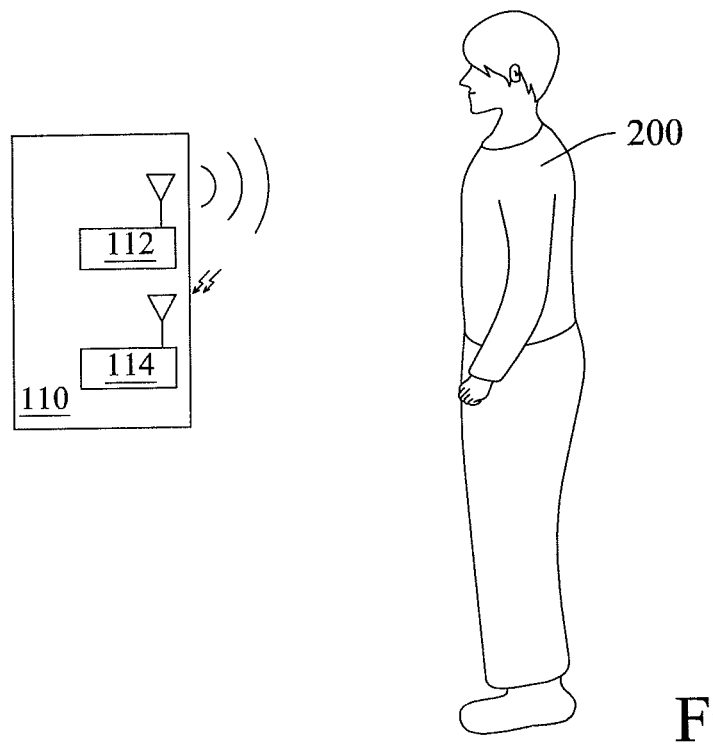
FIG. 6 is a schematic diagram illustrating a measuring unit according to an embodiment of the present invention.
Figure 7:
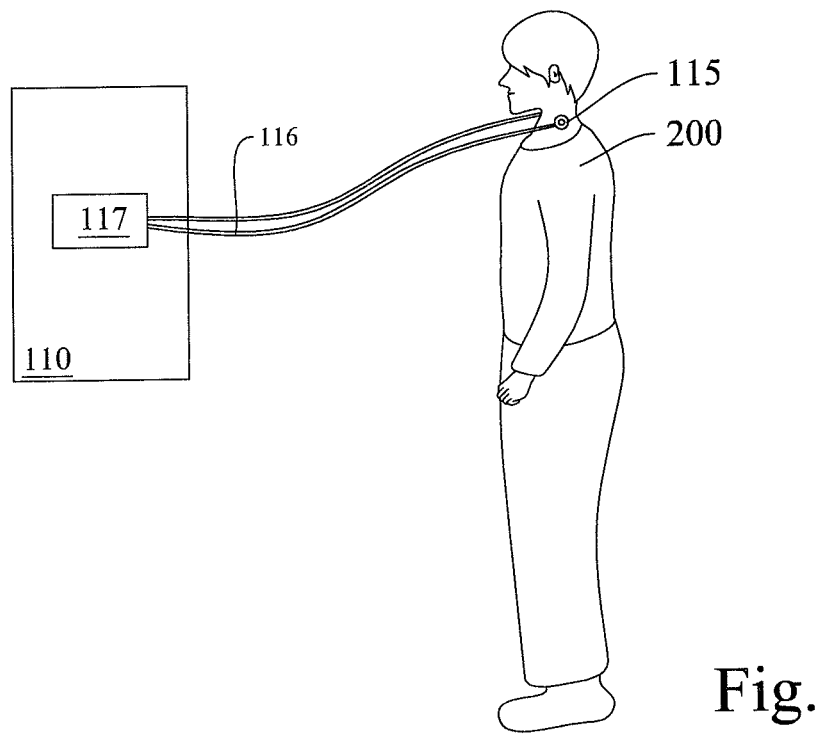
FIG. 7 is a schematic diagram illustrating a measuring unit according to another embodiment of the present invention.

Continuing the description above, the measuring unit 100 can be wireless means and wire means. As shown in FIG. 6 according to one embodiment, the measuring unit 110 comprises: an ultra-wideband emitter 112, for emitting an ultra-wideband signal; and a receiver 114, for receiving a reflected signal of the ultra-wideband signal from the user 200 and obtaining pulse frequency of cardiovascular circulation (e.g. heart rate, pulse rate) in the continuous time. In another embodiment as shown in the FIG. 7, a measuring unit 110 comprises a sensor 115, a transmission cable 116 and a receiver 117 for measuring a feature sequence by wire means, wherein the sensor 116 senses the feature sequence by directly contacting with the user 200; a transmission cable, connected to the sensor 117, for transmitting the feature sequence; and a receiver, for receiving the feature sequence in the continuous time. It should be understood that FIG. 6 and FIG. 7 are only schematic drawings of a specific embodiment but are not drawn to scale while the invention is not to be limited to the particular form disclosed.

For better illustrating the concept of the present invention, a practical example of a commercial product will be described here. A prototype DFD-100 developed by HOLUX operates based on UWB radar to detect users' heart movement. From research studies, the process from awake to sleep can be divided into five stages: (1) awake; (2) first sign of hypo-vigilance and fatigue; (3) strong fatigue; (4) nearly falling asleep including microsleep; and (5) sleep. The aim of the DFD-100 alarm is to warn drivers in early stages of hypo-vigilance and fatigue (stage 2 and 3). This early alert mechanism enables drivers to be conscious that they are sleepy and can promptly react to prevent risk.

The algorithm developed in DFD-100 is verified through road testing. A long-distance commercial bus company agreed to verify the hypo-vigilance algorithm. The testing protocol shows as follows:
1. 3 drivers, up to 16 driving hour a day, 5 days.
2. Average driving distance: 600 km (550 km/highway; 50 km/normal).
3. The bus is equipped with DFD-100 alarm and lane departure sensor (LD sensor) to detect lane departure, tailing distance, braking, steering as well as video camera to record activities of the driver and passengers.
4. All the above data could be saved and transmitted in real-time to control center.
5. False or True Alarms are confirmed not only by the driver himself but also by the video recording aiming toward the drivers.

Comparing results of DFD-100 and LD sensor are shown in Table 1.

According to aforementioned description, one characteristic of the present invention is that physiological features of users measured via non-contact means (e.g. electromagnetic wave technique) can be used for detecting fatigue. Moreover, determining fatigue level of users based on fluctuation of physiological feature data measured by the device of the present invention and warning users while losing concentration can effectively prevent users from accidents. Additionally, usage of the device for detecting fatigue of the present invention is convenient by simply arranging it on clothes near the heart or arteries in human vascular system.

In summary, the method and device of the present invention can analyze and interpret rate of drop and the difference of the rate of drop based on the physiological feature data measured by the device to detect fatigue level of users.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit and scope of the appended claims.

TABLE 2

| Company | HOLUX | Seeing Machines | ASP | Mercedes-Benz/BOSCH |
|---|---|---|---|---|
| Model | DFD-100 | DSS | Anti Sleep Pilot | Attention Assist |
| Country | Taiwan | Australia | Denmark | Germany |
| Primary Sensor Technology | UWB Radar | Visual/Camera | None | Steering, Braking, acceleration Sensors |
| Object to be detected | Driver | Driver | Driver | Vehicle |
| Primary Measures | Heart rate variation | Eye closure/blinking | Reaction time of driver | Steering, Braking, acceleration |

TABLE 1

| ×10 sec | 20 | 40 | 60 | 80 | 100 | 120 | 140 | 160 | 180 | 200 | 220 | 240 | 260 | 280 | 300 | 320 | 340 | 360 | 380 |
|---|---|---|---|---|---|---|---|---|---|---|---|---|---|---|---|---|---|---|---|
| Alarm Status | | | | | | | | | | | | | | | | | | | |
| LD | | A | A | | A | | | | | | | A | A | | | A | A | A | A |
| DFD | | | | | | | | A | A | | | | | | A | | | | |
| Video Recording Verify | | | | | | | | | | | | | | | | | | | |
| LD | | FP | FP | | FP | | | FN | FN | | | FP | FP | | | FP | FP | FP | FP |
| DFD | | | | | | | | T | T | | | | | | FP | | | | |

| ×10 sec | 400 | 420 | 440 | 460 | 480 | 500 | 520 | 540 | 560 | 580 | 600 | 620 | 640 | 660 | 680 | 700 | 720 | 740 | 760 |
|---|---|---|---|---|---|---|---|---|---|---|---|---|---|---|---|---|---|---|---|
| Alarm Status | | | | | | | | | | | | | | | | | | | |
| LD | | A | | A | | A | A | | | | | | | | | | | | |
| DFD | | | | | | | A | A | | | | A | | | A | A | | A | A |
| Video Recording Verify | | | | | | | | | | | | | | | | | | | |
| LD | | FP | | FP | | T | T | | | | | FN | | | FN | FN | | FN | FN |
| DFD | | | | | | T | T | | | | | T | | | T | T | | T | T |

A = Alarming
T = True Alarm
FP = False Positive
FN = False Negative

From Table 1, it could be seen that alarms given by DFD-100 mostly conform to real fatigue condition. On the contrary, the LD sensor obviously gives more false alarms. That is to say, DFD-100 provides more precise and satisfying results that drivers can rely on.

Table 2 displays different types of fatigue detecting devices from different companies.

What is claimed is:
1. A method for detecting fatigue comprising the following steps:
  obtaining a plurality of physiological feature data of a user from a device in continuous time to generate a feature sequence;
  computing a feature curve based on the feature sequence;
  computing a rate of drop based on the feature curve;

determining whether a first condition is met, wherein the first condition is that the rate of drop is larger than a threshold for a first duration;

determining the fatigue level of the user depending on the first condition;

calculating a difference of rate of drops;

determining whether a second condition is met, wherein the second condition is that the difference falls within a threshold interval for a second duration; and determining the fatigue level of the user depending on the first condition and the second condition, wherein a second warning message is generated when the first condition and the second condition are met.

2. The method for detecting fatigue according to claim 1, wherein the rate of drop is an average slope counted per minute; and the threshold of the first condition is less than −0.05 and the first duration is greater than 150 seconds.

3. The method for detecting fatigue according to claim 2, wherein a warning message is generated when the first condition is met.

4. The method for detecting fatigue according to claim 1, wherein the rate of drop is an average slope counted per five minutes; and the threshold of the first condition is less than 0 and the first duration is equal or greater than 140 seconds.

5. The method for detecting fatigue according to claim 4, wherein the threshold interval of the second condition is greater than −0.001 and less than 0.004.

6. The method for detecting fatigue according to claim 5, wherein the second duration is equal or greater than 60 seconds.

7. The method for detecting fatigue according to claim 1, further comprising:

determining whether a third condition is met, wherein the third condition is that the difference falls within the threshold interval for a third duration; and determining the fatigue level of the user depending on the first condition, the second condition and the third condition, wherein when the first condition and the third condition are met, a third warning message is generated.

8. The method for detecting fatigue according to claim 7, wherein the third duration is at least 30 seconds greater than the second duration and the threshold interval is greater than −0.001 and less than 0.004.

9. The method for detecting fatigue according to claim 1, wherein the feature sequence comprises data representative of heart rate per minute updated every second measured from the user or data representative of pulse rate per minute updated every second measured from the user.

10. A device for detecting fatigue comprising:

a measuring unit, for measuring a plurality of physiological feature data from a user in continuous time to generate a feature sequence;

a memory unit, for storing the feature sequence;

a computing unit electrically connected to the measuring unit and the memory unit, for computing a feature curve based on the feature sequence and computing a rate of drop based on the feature curve; and the computing unit determining whether a first condition is met for obtaining a detection result of the fatigue level of the user, wherein the first condition is that the rate of drop is larger than the threshold for a first duration; and an output unit electrically connected to the computing unit, for outputting the detection result of the fatigue level;

calculating a difference of the rate of drops; and determining whether a second condition is met, for obtaining the detection result of the fatigue level of the user, wherein the second condition is that the difference falls within a threshold interval for a second duration.

11. The device for detecting fatigue according to claim 10, wherein the measuring unit can be wire or wireless means.

12. The device for detecting fatigue according to claim 11, wherein the measuring unit operates by wireless means, comprising:

an ultra-wideband emitter, for emitting a ultra-wideband signal; and a receiver, for receiving a reflected signal of the ultra-wideband signal reflected from the user and receiving the physiological feature data in the continuous time to generate the feature sequence.

13. The device for detecting fatigue according to claim 11, wherein the measuring unit operates by wire means, comprising:

a sensor, for sensing a physiological feature signal by contacting with the user;

a transmission cable connected to the sensor, for transmitting the physiological feature data; and a receiver, for receiving the physiological feature data in the continuous time to generate the feature sequence.

14. The device for detecting fatigue according to claim 10, wherein the feature sequence comprises data representative of heart rate per minute updated every second measured from the user or data representative of pulse rate per minute updated every second measured from the user.

15. The device for detecting fatigue according to claim 10, wherein the rate of drop is average slope counted per minute; and the threshold of the first condition is less than −0.05 and the first duration is equal or greater than 150 seconds.

16. The device for detecting fatigue according to claim 15, wherein a first warning message is generated when the first condition is met.

17. The device for detecting fatigue according to claim 10, wherein the rate of drop is an average slope counted per five minutes; and the threshold of the first condition is less than 0 and the first duration is equal or greater than 140 seconds.

18. The device for detecting fatigue according to claim 17, wherein the second condition is that the threshold interval is greater than −0.001 and less than 0.004.

19. The device for detecting fatigue according to claim 18, wherein the second duration is equal or greater than 60 seconds.

20. The device for detecting fatigue according to claim 10, wherein a second warning message is generated when the first condition and the second condition are met.

21. The device for detecting fatigue according to claim 10, wherein the computing unit further comprises:

determining whether a third condition is met, for obtaining the detection result of the fatigue level of the user, wherein the third condition is that the difference falls within the threshold interval for a third duration.

22. The device for detecting the fatigue according to claim 21, wherein the third duration is at least 30 seconds greater than the second duration and the threshold interval is greater than −0.001 and less than 0.004.

23. The device for detecting the fatigue according to claim 22, wherein a third warning message is generated when the first condition and the third condition are met.

24. The device for detecting fatigue according to claim 10, wherein the output unit is at least one of a display screen or an audio device.

* * * * *